United States Patent [19]

Glasscock et al.

[11] Patent Number: 5,633,168
[45] Date of Patent: May 27, 1997

[54] CONTROLLED DISPERSION FLOW ANALYSIS SYSTEM

[76] Inventors: Larry M. Glasscock, 801 Second Ave., Cullman, Ala. 35055; Alice Glasscock, 3224 No. 3 Country Club Rd., Birmingham, Ala. 35213; Krishnaji R. Kulkarni, 1015-C Beacon Pkwy. E., Birmingham; David W. Garber, 1621 Valley Ave., Apt. 3E, Homewood, both of Ala. 35209

[21] Appl. No.: 487,839

[22] Filed: Jun. 7, 1995

[51] Int. Cl.$^6$ .................................................. G01N 35/08
[52] U.S. Cl. ........................... 436/52; 436/47; 436/48; 436/71; 436/174; 436/177; 422/64; 422/65; 422/66; 422/67; 422/68.1; 422/81; 422/82; 422/82.09; 422/110
[58] Field of Search ................................ 436/47, 48, 52, 436/71, 174, 177; 422/64, 65, 66, 67, 68.1, 81, 82, 82.09, 110

[56] References Cited

U.S. PATENT DOCUMENTS

| | | | |
|---|---|---|---|
| 4,022,575 | 5/1977 | Hansen et al. | 23/230 R |
| 4,071,324 | 1/1978 | Reid | 23/288 K |
| 4,135,881 | 1/1979 | Bakx et al. | 23/230 PC |
| 4,224,033 | 9/1980 | Hansen et al. | 23/230 R |
| 4,314,824 | 2/1982 | Hansen et al. | 23/230 R |
| 4,520,108 | 5/1985 | Yoshida et al. | 436/52 |
| 4,595,496 | 6/1986 | Carson | 210/101 |
| 4,610,544 | 9/1986 | Riley | 422/64 |
| 4,742,716 | 5/1988 | Ruzicka et al. | 73/864.81 |
| 4,952,372 | 8/1990 | Huber | 422/81 |
| 5,080,866 | 1/1992 | Petty et al. | 422/80 |
| 5,105,851 | 4/1992 | Fogelman | 137/625.11 |
| 5,108,928 | 4/1992 | Menard et al. | 436/43 |
| 5,171,530 | 12/1992 | Pennatto | 422/63 |
| 5,221,519 | 6/1993 | Wuerschum | 436/47 |
| 5,240,856 | 8/1993 | Goffe et al. | 435/299 |
| 5,262,049 | 11/1993 | Ferkany | 436/47 |
| 5,284,773 | 2/1994 | Kulkarni et al. | 436/52 |
| 5,286,652 | 2/1994 | James et al. | 422/64 |
| 5,384,093 | 1/1995 | Ootani et al. | 436/47 |
| 5,456,882 | 10/1995 | Covain | 436/47 |
| 5,468,643 | 11/1995 | Su et al. | 436/172 |

OTHER PUBLICATIONS

Kulkarni et al. "Quantification of cholesterol in all lipoprotein classes by the VAP–II method"— Journal of Lipid Research vol. 35, 1994 159–168.

Primary Examiner—Jill Warden
Assistant Examiner—Sharidan Carrillo
Attorney, Agent, or Firm—David E. Bennett; Rhodes, Coats & Bennett, L.L.P.

[57] ABSTRACT continuous flow analysis system measures the cholesterol distribution among different lipoprotein classes in a blood sample. A blood plasma sample is separated into different lipoprotein classes by single vertical spin density gradient ultracentrifugation. The sample is then introduced in a continuous succession into a reagent stream which flows continuously through a detector. A sensor detects the end of the sample in a sample stream before it is introduced into said reagent stream. A wash solution is introduced into the sample stream in response to detection of the end of said sample. The wash solution back flows through the sample stream into the sample container to wash any residue and/or air bubbles from the sample stream. After a predetermined time period, the sample stream is closed and the process is repeated for the next sample.

21 Claims, 5 Drawing Sheets

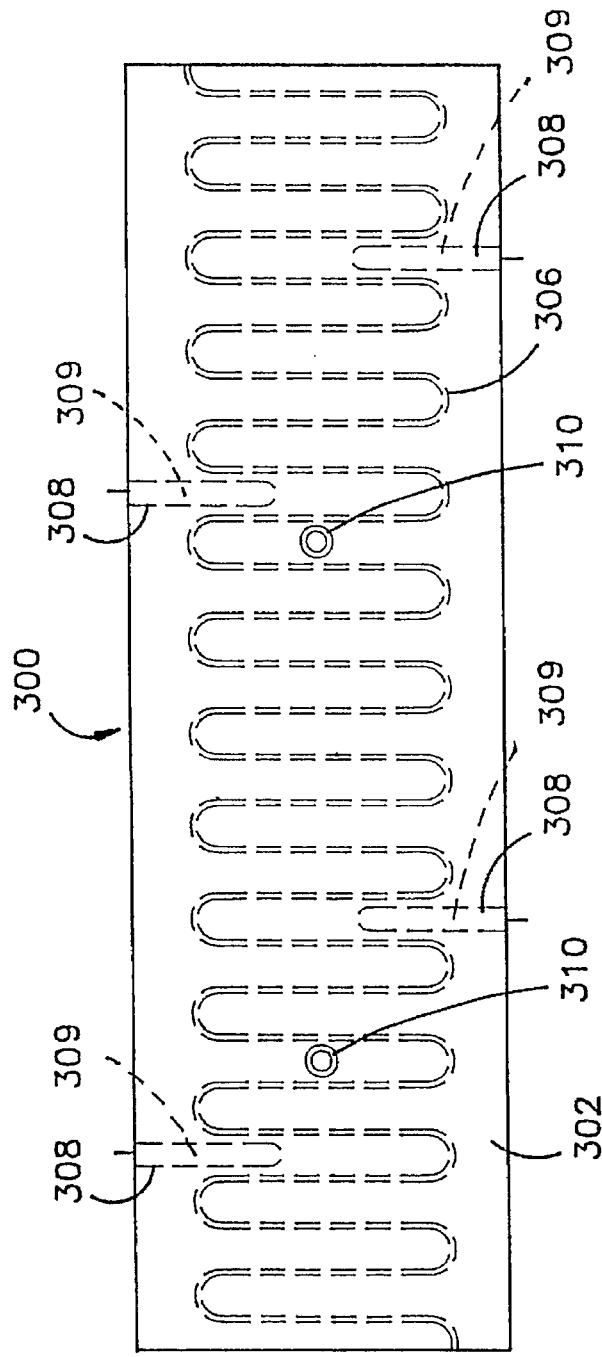
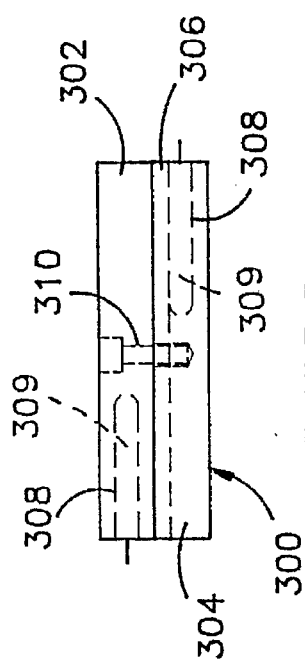
FIGURE 2
FIGURE 3

CONTROLLED DISPERSION FLOW ANALYSIS SYSTEM

BACKGROUND OF THE INVENTION

The present invention relates generally to a method and apparatus for determining the concentrations of lipoproteins in blood using a continuous flow analyzer.

It is well-known that total serum cholesterol is strongly correlated with the incidence of atherosclerosis and coronary heart disease. More recent studies also indicate that specific fractions of cholesterol are more closely associated with coronary heart disease than others. Recent studies have implicated LDL (low density lipoprotein) as the class of lipoprotein responsible for the accumulation of cholesterol in cells, whereas HDL (high density lipoprotein) has been shown to be important in the removal of excess cholesterol from cells. Thus, increased levels of LDL cholesterol have been associated with the greater risk of coronary heart disease, while a strong inverse relationship exists between HDL cholesterol and the risk of coronary heart disease.

In addition to LDL and HDL, several other lipoproteins have been shown to represent independent risk factors for coronary heart disease. Increased plasma concentrations of lipoprotein(a) [Lp(a)], a cholesterol rich lipoprotein, has been observed in survivors of myocardial infarction. One study, which reports the relationship of levels of Lp(a) and coronary heart disease in patients who underwent coronary angiography, concluded that plasma Lp(a) appears to be a major independent risk factor for coronary heart disease. Elevation of plasma VLDL is seen in survivors of myocardial infarction, suggesting the possible involvement of this lipoprotein in the atheroschlerotic process.

Measurement of total cholesterol alone may not be adequate to identify subjects at risk for coronary heart disease. An individual with normal or near normal levels of total cholesterol may still be at risk because of low HDL levels, elevated Lp(a) levels, or elevated levels of VLDL. Moreover, the predictive power of total cholesterol for risk of coronary heart disease diminishes in men with increasing age. Therefore, assessment of the distribution of cholesterol among all the lipoproteins (a lipoprotein cholesterol profile), in addition to total cholesterol, is desirable in order to accurately assess risk for coronary heart disease.

Methods currently used to determine the concentration of cholesterol in the different lipoprotein classes can be divided into direct methods and indirect methods. In direct methods, lipoprotein cholesterol is determined by enzymatic assay of the individual lipoproteins, which are separated by ultracentrifugation, electrophoresis, or selective precipitation. The most accurate of these methods involves ultracentrifugation. However, ultracentrifugation separation methods are expensive, time-consuming, and are not practicable for clinical applications wherein multiple analyses are carried out in large numbers.

Another method of determination of cholesterol distribution among plasma lipoproteins involves the separation of lipoproteins by high performance liquid chromotography and the on-line detection of cholesterol in the postcolumn effluent using an enzymatic reagent. This method also provides a direct measure of lipoprotein cholesterol. However, this method requires a relatively long retention period of separation of the sample. Moreover, the separation technique results in some loss of lipoproteins which could result in an underestimation of cholesterol concentration.

Indirect methods, as a general rule, are better suited for clinical applications than are direct methods. The most commonly used method for measurements of lipoprotein cholesterol performs multiple analyses using different aliquots of the same plasma sample. Total cholesterol (TC) is measured using a first aliquot of the sample. In a second aliquot, VLDL and LDL are removed by precipitation and the supernatant is assayed for cholesterol to provide a measure of HDL cholesterol. An estimate of LDL is obtained by measuring the triglycerides (TG) in a third aliquot using the Friedewald formula or is measured directly after ultracentrifugal isolation of very low density lipoprotein. The LDL cholesterol concentration is not measured directly, but is calculated by subtracting the HDL cholesterol and VLDL cholesterol values from the total cholesterol.

Although this method is relatively rapid and inexpensive, there are several steps where error could be introduced. For example, accurate measurements of HDL depends on complete precipitation of apo-B containing lipoproteins. Traces of LDL in the supernatant can lead to overestimation of HDL cholesterol. Moreover, the multiple assumptions involved in the Friedewald formula make this method susceptible to error. In addition, this method does not provide a separate measure of IDL cholesterol or Lp(a) cholesterol. Instead, these values are included in the LDL cholesterol measurement.

The VAP method (Vertical Auto Profile) provides a direct method for determination of lipoprotein concentrations. The VAP method uses short spin density gradient vertical ultracentrifugation to separate the classes of lipoproteins. Analysis of cholesterol is made using an air segmented continuous flow analysis system to provide a lipoprotein cholesterol profile. The VAP method provides a direct measure of lipoprotein cholesterol using a single aliquot of plasma. However, VAP requires a relatively large sample (1.3 ml), and the equipment used in the VAP method is cumbersome, making its operation and maintenance difficult. Furthermore, this method causes overlapping of adjacent lipoprotein peaks in the cholesterol profile resulting in a substantial loss of resolution. Quantification of Lp(a) and IDL, which are not well-separated from other lipoproteins by density-gradient centrifugation becomes difficult particularly when present in small amounts.

An improvement of the original VAP method, known as the VAP II method, provides a direct method for determination of lipoprotein concentrations which is suitable for clinical applications. The VAP II method, like the VAP method, uses short spin density gradient vertical ultracentrifugation to separate the classes of lipoproteins. The separated sample is then introduced into a continuous flow analysis system to provide a profile of the cholesterol concentration in all lipoprotein classes. However, in contrast to the VAP method, the VAP II method continuously introduces the entire blood plasma sample into a non-segmented carrier stream while controlling dispersion of the sample. The VAP II method is described in U.S. Pat. No. 5,284,773, which is incorporated herein by reference. The VAP II method requires comparatively small samples of blood and is rapid enough to be used in large-scale population screening. However, the VAP II method in its current form requires highly skilled technicians to monitor the testing procedures, and requires human intervention at numerous points during the process. Therefore, there still remains a need for a more automated testing procedure which eliminates the need for human intervention, and which can be carried out by other than highly skilled lab technicians.

SUMMARY AND OBJECTS OF THE INVENTION

The present invention is a controlled dispersion flow analysis system for direct quantitation of cholesterol in all lipoprotein classes. A blood plasma sample is placed in a tube and subjected to single vertical spin gradient density ultracentrifugation to separate the lipoproteins in the blood plasma sample. The separated sample is then introduced into a controlled dispersion flow analysis system which provides a profile of the cholesterol concentrations in all lipoprotein classes.

The controlled dispersion flow analysis system consists of a tube-piercing needle assembly for piercing a sample tube containing the blood plasma sample, a flow control unit for mixing the sample with a continuous, non-segmented reagent stream, a reaction unit for reacting the sample with the reagent to produce a reaction signal, a detector for monitoring the reaction signal, and a computer for storing and analyzing the reaction signal data. The reaction signal data is decomposed by the computer to make a quantitative determination of cholesterol in all lipoprotein classes.

The flow control system is designed to allow fully automated control of all test fluids once the test procedure has been initiated. The flow control unit includes a first valve for controlling the flow of a saline solution which is used to establish a baseline for measuring cholesterol concentrations. The first valve is normally open at the beginning of the test procedure. A second valve controls the flow of the blood plasma sample through the flow control unit. The second valve is normally closed to begin the test procedure. A sensor is disposed between the second valve and the sample container to detect the end of the sample.

An electrical controller selectively opens and closes the first and second valves during the test procedure. The needle assembly punctures the sample container while the baseline fluid flows through the flow control unit. Once a baseline for measuring cholesterol concentration is established, the first valve is closed to stop the flow of saline solution, and the second valve is opened to start the flow of sample through the flow control unit. The sample is mixed with a reagent and forms a reaction mixture which passes through a detector which measures the absorbance of the reaction mixture. The entire sample is introduced continuously without any segmentation of the sample. Thus, the absorbance data produces a cholesterol profile which can be decomposed to determine the cholesterol concentration of each individual lipoprotein class.

When the sensor detects the end of the sample, the first valve is opened to start the flow of saline solution into the control unit. The second valve remains open for a predetermined time period so that the saline solution back flows into the sample container to wash out any residue or air bubbles in the sample drain line. After the predetermined time period has elapsed, the second valve closes to end the process cycle. The process is then repeated for each sample.

In another aspect of the present invention, an automatic tube positioning and puncturing assembly is provided for automatically feeding samples into the flow control unit. The tube positioning and puncturing assembly comprises a tube fixture having a plurality of wells for receiving the sample tubes. In one embodiment of the automatic tube positioning and puncturing assembly, a stationary fixture is used having a tube-piercing needle in each tube well which punctures the sample tube when it is inserted into the tube well. Each needle assembly is connected to a respective inlet of a rotary valve which indexes to feed each sample, one at a time, into the flow control unit. In a second embodiment of the tube positioning and puncturing assembly, a movable fixture is used. In this embodiment, the needle assembly is movable between an extended and retracted position. At the beginning of the process, the tube fixture is positioned such that the first sample tube is aligned with the needle. The needle is extended to puncture the first sample tube and feed the sample into the flow control unit. After the first sample is tested, the needle retracts, the tube fixture indexes to the next tube and the process is repeated.

Based on the foregoing, it is a primary object of the present invention to provide a rapid, simple, and relatively inexpensive apparatus for direct analysis of cholesterol in all lipoprotein classes.

Another object of the present invention is to provide a diagnostic method for direct analysis of cholesterol which is suitable for clinical application.

Still another object of the present invention is to provide a diagnostic method for direct analysis of cholesterol which minimizes the need for human intervention during the testing process.

BRIEF DESCRIPTION OF THE DRAWINGS

FIG. 2 is a plan view of a reaction unit used in connection with the controlled dispersion flow analysis system.

FIG. 3 is an end view of the reaction unit.

DETAILED DESCRIPTION OF THE INVENTION

Figure 1:
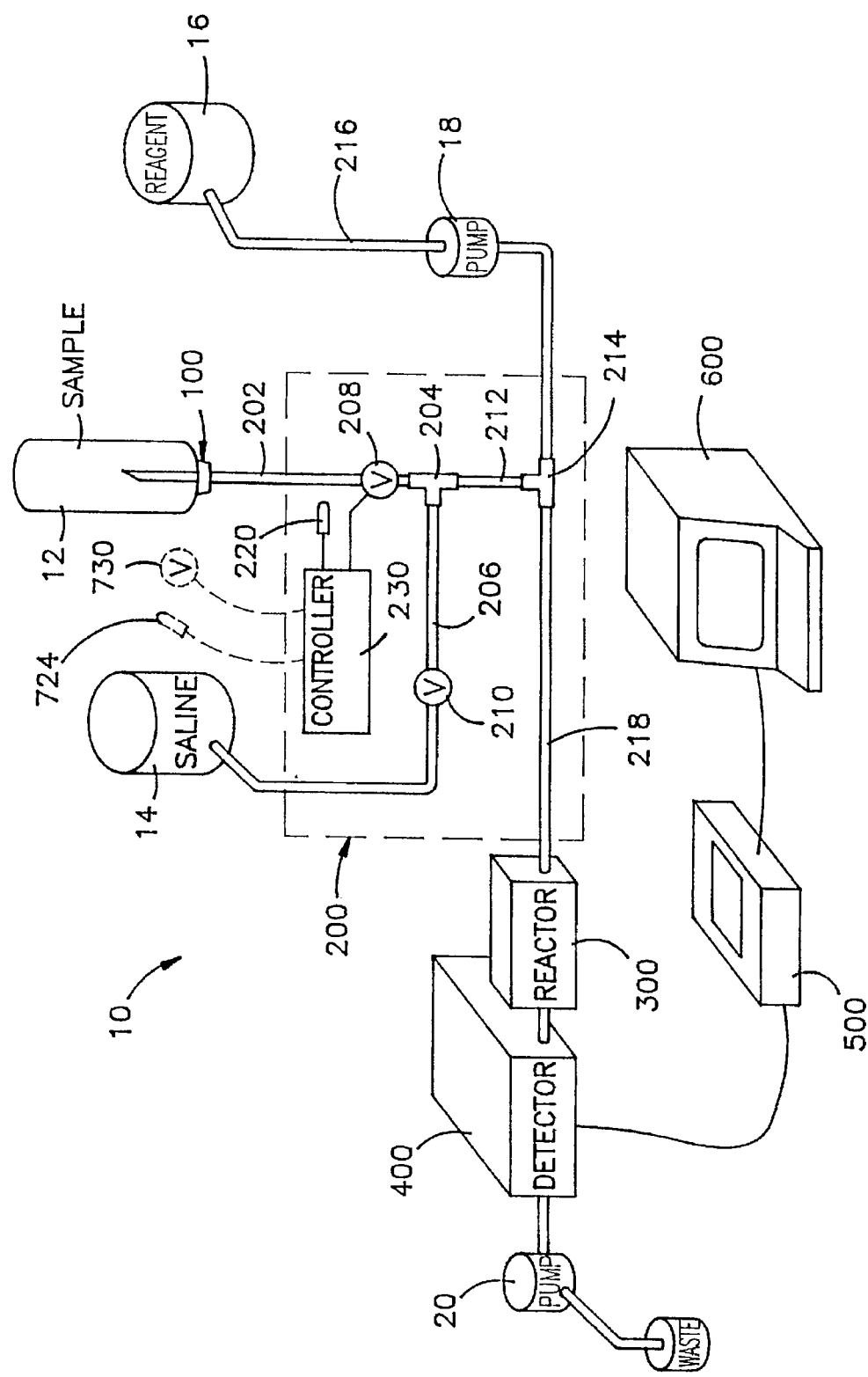
FIG. 1 is a schematic illustration of the controlled dispersion flow analysis system of the present invention.

Referring now to the drawings, and particularly to FIG. 1, there is shown a schematic illustration of the controlled dispersion flow analysis system which is indicated generally by the numeral 10. The controlled dispersion flow analysis system 10 includes a tube-piercing needle assembly 100 for piercing a sample tube containing a blood plasma sample which has been separated into individual lipoprotein classes by ultracentrifugation; a flow control sub-system 200 for mixing the sample with a continuous, non-segmented reagent stream; a reaction unit 300 for reacting the sample with the reagent to produce a reaction signal indicative of the cholesterol concentration in the sample; a detector 400 for monitoring the reaction signal; a chart recorder 500 for recording the cholesterol profile; and a computer 600 for collecting and analyzing absorbance data.

The needle assembly 100 is used to puncture a sample tube 12 and to feed the sample to the flow control sub-system 200. The needle assembly 100 can be any commercially available flow through needle. A saline reservoir 14 and reagent reservoir 16 are also connected to the flow control sub-system 200. A peristaltic pump 18 provides a continuous, non-segmented stream of reagent to the flow control subsystem 200 throughout the test cycle. A second peristaltic pump 20 is disposed downstream of the detector 400. The second peristaltic pump 20 is operated at a higher rate than the first peristaltic pump 18 to induce the saline solution and sample into the flow control sub-system 200.

During operation, the flow control sub-system 200 selectively controls the flow of saline solution and sample. Initially, saline solution is allowed to flow through the flow control sub-system 200 to mix with the reagent. The saline solution is used to establish a baseline. After a predetermined period of time, the flow of saline solution is stopped and the sample is fed into the flow control sub-system 200. The sample mixes with the reagent and flows through the reaction unit 300 and then to the detector 400 which measures a characteristic of the reaction mixture to determine the cholesterol concentration in the sample.

The flow control sub-system 200 includes a sample supply line 202 which connects the needle assembly 100 to one input of a Y-connector 204. The Y-connector 204 has two inputs and one output. The opposing input of the Y-connector 204 is connected by a supply line 206 to the saline reservoir 14. Supply line 202 passes through a first pinch valve 208 used to selectively start and stop the flow of fluid from the sample tube. A second pinch valve 210 is used to selectively start and stop the flow of saline solution from reservoir 14. The outlet of the Y-connector 204 is connected by an outlet line 212 to a second Y-connector 214. Connector 214 also includes two inputs and one output. Also connected to the Y-connector 214 is a reagent supply line 216 for supplying a continuous, non-segmented stream of reagent. The outlet of the connector 214 is connected by a reaction tube 218 to the reaction unit 300. From the reaction unit 300, the fluid flows through a detector 400 which measures the absorbance of the mixture passing through the detector 400. The recorder 500 records the absorbance in the form of a graph while the computer 600 stores and analyzes the absorbance data.

The flow control sub-system 200 is controlled by an electrical controller 230. The electrical controller 230 may be either a programmable controller or an equivalent hardwired electrical circuit. The electrical controller receives input from a sensor 220 which detects the end of the sample as it enters the flow control sub-system 200. The outputs of the electrical controller are used to control the pinch valves 208 and 210.

During an analysis, reagent flows continuously through the flow control subsystem 200. The plasma sample and saline solution are delivered at selected points in the analysis. The flow control sub-system 200 allows automatic switching between delivery of sample and saline solution at appropriate times in the analysis.

The reaction unit 300, shown in FIGS. 2 and 3, comprises two metal blocks 302 and 304 made preferably from aluminum or titanium. One block 304 contains a serpentine groove 306 in its mating surface to accommodate the reaction tube 218, which is preferably a 0.8 mm inside diameter Teflon tube approximately two meters in length. The mating block 300 will have a flat mating surface. The blocks 302 and 304 are secured together by a securing bolt 310 which extends through a hole in the upper block 302 and screws into a threaded hole in the lower block 304. Each block 302 and 304 includes two bores 308 to receive electric cartridge heaters 309. The cartridge heaters 309 are located to provide an even distribution of heat throughout the metal blocks 302 and 304. The temperature is monitored by a thermocouple and a controller varies the voltage to the cartridge heaters 309 to regulate the temperature. The reaction unit 300 heats the reaction mixture as it flows through the reaction tube 218 toward the detector 400.

Figure 7:
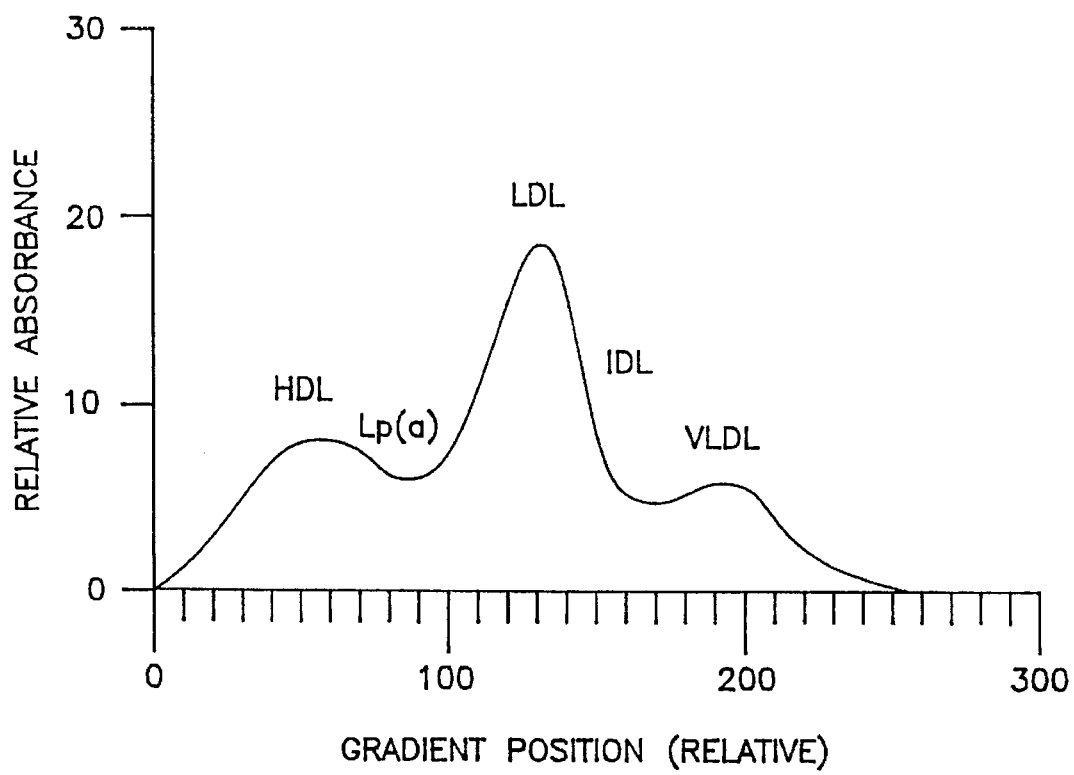
FIG. 7 is a typical cholesterol profile produced in accordance with the present invention.

The detector 400 is disposed downstream from the reaction unit 300. The detector 400 comprises a spectrophotometer which measures the absorbance of the reaction mixture as it passes through the detector 400. The absorbance is measured at 505 nm. The chart recorder 500 records the reaction signal measured by the detector 400 to produce a cholesterol profile while the computer 600 collects the absorbance data. A typical absorbance curve or cholesterol profile is illustrated in FIG. 7. Each point on the absorbance curve corresponds to the concentration of cholesterol in the blood plasma sample. The cholesterol profile is decomposed by the computer 600 to determine the cholesterol concentration associated with each class of lipoproteins.

Figure 4:
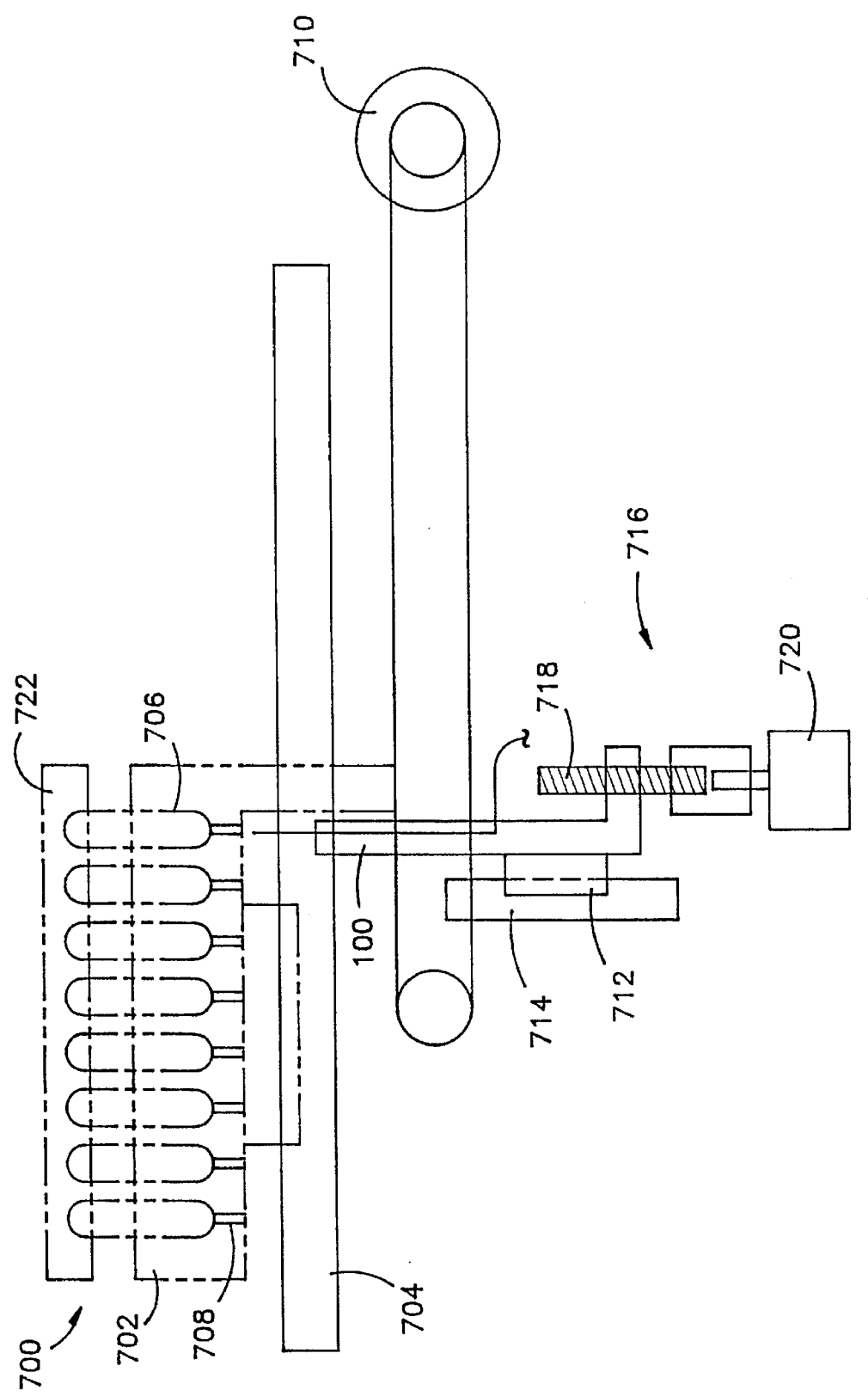
FIG. 4 is an elevation view of a first embodiment of the tube positioning and puncturing assembly.

The controlled dispersion flow apparatus 10 of the present invention may also include an automatic tube positioning and puncturing assembly 700. FIG. 4 shows one embodiment of a tube positioning and puncturing assembly to allow for more automated sampling. As shown in FIG. 4, a tube fixture 702 is slidably mounted on a linear bearing track 704. The tube fixture 702 includes a plurality of tube wells 706 for receiving sample tubes containing the blood plasma samples. A needle hole 708 extends from the bottom of the tube fixture 702 to each of the tube wells 706.

The tube fixture 702 is driven by a stepper motor 710 to position the sample tubes with respect to the needle assembly 100. The needle assembly 100 is mounted on a carriage 712 which slides vertically along a second linear bearing track 714. The carriage 712 is driven by a ball drive mechanism 716 including a ball screw 718 and stepper motor 720 to move the needle assembly 100 between an extended position and a retracted position.

In operation, the stepper motor 720 positions the tube fixture 702 such that the first tube is aligned with the needle assembly 100. A sensor 724 (See FIG. 1) checks to determine if a tube is present in the fixture 702, and, if so, the ball drive mechanism 716 is actuated to extend the needle assembly 100. As the needle assembly 100 is extended, it passes through the needle hole 708 in the tube fixture 702 and punctures the sample tube. A hold-down cap 722 holds the sample tubes down as the tubes are punctured by the needle assembly 100. The flow control sub-system 200 will then begin its automatic sequence as described below. In a preferred embodiment of the invention, the programmable controller is responsive to the signal from sensor 724 to close valve 210 and open valve 208 to start the flow of the blood sample. When the cycle is complete, the tube fixture 702 is indexed and the process is repeated until all samples have been tested.

Figure 6:
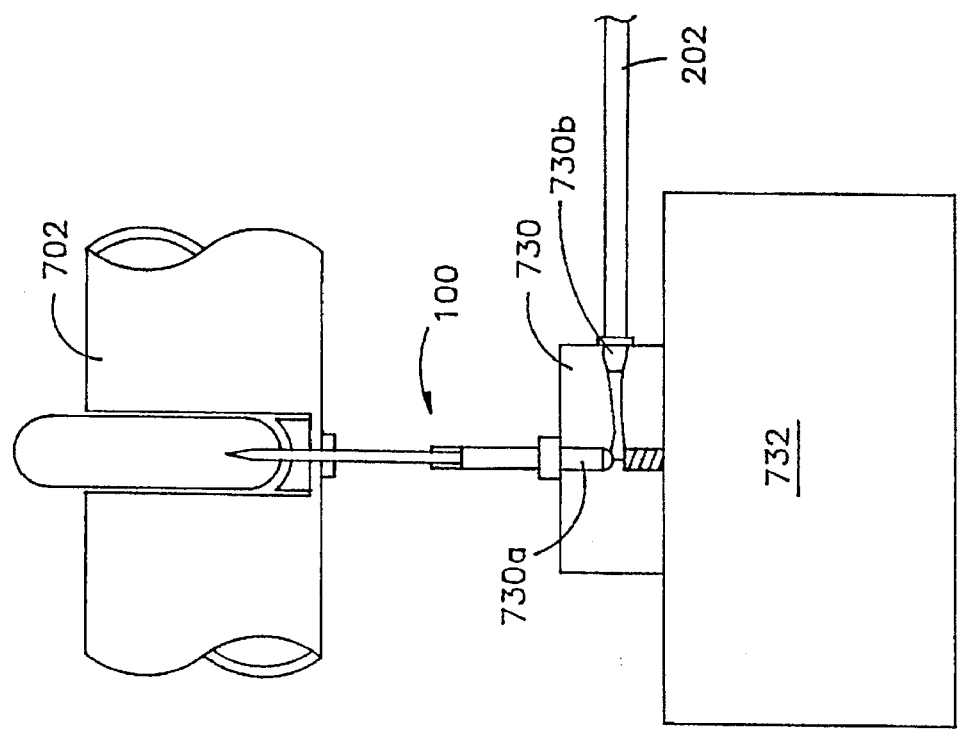
FIG. 6 is a partial sectional view of the second embodiment of the tube positioning and puncturing assembly.
Figure 5:
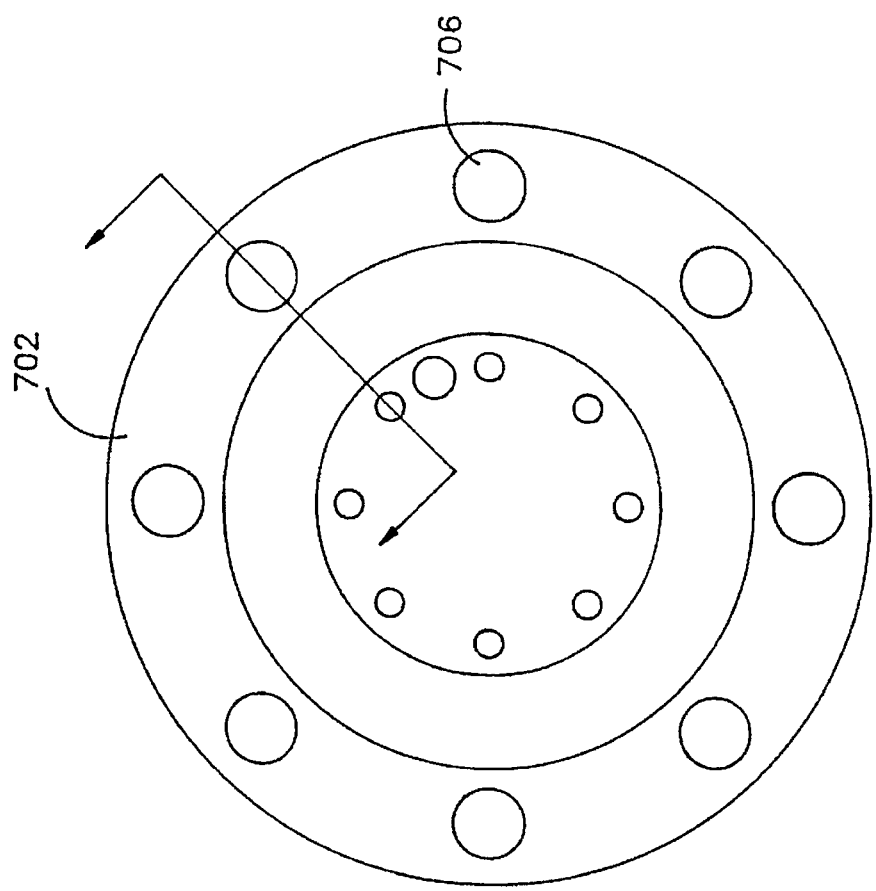
FIG. 5 is a plan view of a second embodiment of the tube positioning and puncturing assembly.

FIGS. 5 and 6 show an alternate embodiment of the tube positioning and puncturing assembly. The tube fixture 702 is circular and has eight tube wells 706 equally spaced around its circumference. Eight individual needle assemblies 100 are fixed in respective tube wells 706 in the tube fixture 702. Each needle assembly 100 is communicatively connected to a respective inlet of an eight-position rotary valve 730 having eight inlets 730a and one outlet 730b. The outlet 730b of the valve 730 is connected to sample supply line 202 and feeds the sample into the flow control sub-system 200. The needle assemblies 100 pierce their corresponding sample tubes as the tubes are inserted into the fixture 702. An electric actuator 732 indexes the rotary valve 730 to feed each sample, one at a time, into the flow control sub-system 200 which then begins its automatic sequence. After each cycle is completed, the rotary valve 730 indexes to the next position to repeat the process until all eight samples are tested.

Prior to analysis of the plasma samples, the cholesterol reagent is prepared and placed in the reagent reservoir 16.

The cholesterol reagent (high-performance, Boehringr Mannheim Diagnostics) is prepared by dissolving 250 mg/ml of reagent in deionized, distilled water. Brij 35 (Sigma Chemicals) is added to the reagent solution (2.5% C/V) to facilitate lipoprotein particle breakdown. All liquid solutions, including cholesterol reagent solution, are degassed by laboratory vacuum to minimize air bubble formation.

The plasma sample is diluted with a saline EDTA solution (0.9% NaCl, 1 mmol/1 EDTA, pH=7.4, density=1.006 kg/l and then adjusted to a density of 1.21 kg/l by adding dry KBr. A discontinuous gradient is formed in a 2 ml ultracentrifuge tube by first pipetting the saline/EDTA solution (as described above) into a glass Pasteur pipette placed in each tube and then underlaying with density adjusted plasma. The tubes are then filled and placed in a rotor and centrifuged. After centrifugation, the tube is punctured by the needle assembly 100 at the bottom so as not to disturb the formed gradient.

The first stage of the testing process is referred to herein as the baseline stage. During the baseline stage, pinch valve 208 is closed and pinch valve 210 is opened to permit the flow of saline solution through the flow control sub-system 200. The saline solution is mixed with the reagent, which flows continuously through the process, at the Y-connector 214. The saline solution and reagent are blended as they flow through the reaction unit 300 and detector 400. The saline solution provides a baseline against which the cholesterol values are compared. Saline solution is used to establish a baseline because it has a density which closely matches the density at the bottom of the sample gradient and thus avoids any artifact at the baseline due to change in the absorbance caused by change in density of the sample.

At the completion of the baseline stage, pinch valve 208 is opened while pinch valve 210 is simultaneously closed to start the sample drain and stop the flow of saline solution into the flow control sub-system 200. This begins the sample testing phase during which the blood sample flows through the flow control sub-system 200 and continuously mixes with the reagent at connector 214. The sample and reagent form a reaction mixture as it moves through the reaction unit 300. After exiting the reaction unit 300, the reaction mixture flows through the spectrophotometer 400 which measures the absorbance of the reaction mixture at 505 nm. The chart recorder 500 records the absorbance measured by the detector 400 in the form of a graph to produce a cholesterol profile, while the computer 600 stores and analyzes the absorbance data. The computer decomposes the absorbance data to make a quantitative determination of cholesterol in the individual lipoprotein classes.

A meniscus detector 220 senses the end of the sample as the sample drains into the flow control sub-system 200. When the end of the sample is sensed by the meniscus detector 220, ending the sample testing phase, the pinch valve 210 is opened to start the flow of saline solution into the flow control sub-system to begin the cleaning stage. While both valves 208 and. 210 are opened, saline solution backflows through the supply line 202 to flush any air bubbles or residue back into the sample container. To ensure that the saline solution backflows through the sample supply line 202, the saline reservoir 14 can be positioned at a height above the sample container sufficient to create pressure that will cause the saline solution to back flow through supply line 202. When the predetermined time delay elapses, pinch valve 208 closes while valve 210 remains open. Thus, saline solution continues to flow to reestablish the baseline for the next sample.

The controlled dispersion flow analysis system of the present invention provides a reliable method for controlling the flow of fluids during a test procedure. Once the test procedure is initiated, any further human intervention is avoided. Further, compared studies showed that the test results produced in accordance with the present invention are highly correlated with other procedures currently in use in clinical applications.

What is claimed is:

1. An apparatus for measuring the cholesterol distribution among plasma lipoproteins in a blood sample separated into two or more gradients containing said plasma lipoproteins, said apparatus comprising:

a) a reaction tube having an inlet and an outlet;
   b) a reagent supply connected to the inlet of said reaction tube for providing a continuous, non-segmented stream of reagent in said reaction tube;
   c) a fluid sampling circuit for alternately introducing a baseline fluid and said blood plasma sample into said reaction tube to be mixed with said continuous reagent stream, said fluid sampling circuit including:
      i) a first inlet line connected to a source of a baseline fluid;
      ii) a second inlet line connected to a sample container containing said blood plasma sample; and
      iii) an outlet line connected to said reaction tube for alternately feeding said baseline fluid and said blood plasma sample into said reaction tube;
   d) a meniscus detector disposed along said second inlet line for detecting the end of said blood plasma sample;
   e) an electrical controller for selectively controlling the flow of said baseline fluid and said blood plasma sample, said controller programmed to:
      i) open said second inlet line to feed the blood plasma sample into said reaction tube;
      ii) open said first inlet line when the end of said sample is detected by said meniscus detector while said second inlet line remains open to back-flush said second inlet line with said baseline fluid; and
      iii) close said second inlet line a predetermined time period after said first inlet line is opened while said first inlet line remains open to deliver baseline fluid to said reaction tube; and
   f) a detector connected to the outlet of said reaction tube for measuring a characteristic of the fluid flowing through said detector indicative of the cholesterol concentration in said fluid.

2. The measuring apparatus of claim 1 further including a fixture for simultaneously receiving and holding a plurality of sample containers, each of which contains a separate blood plasma sample; and means for automatically and sequentially feeding said blood plasma samples into said fluid sampling circuit.

3. The measuring apparatus of claim 2 further including a needle assembly including a flow-through puncturing needle for puncturing said sample containers in said fixture and feeding said samples into said fluid sampling circuit; and indexing means for indexing said fixture to position said sample tubes in alignment with said needle assembly.

4. The measuring apparatus of claim 3 wherein said needle assembly is movable between an extended position to puncture said sample containers and a retracted position.

5. The measuring apparatus of claim 2 wherein said electrical controller is programmed to close said first inlet line and open said second inlet line to start the flow of said blood plasma sample through said fluid sampling circuit in response to detection of a sample container in said fixture.

6. The measuring apparatus of claim 2 further including sensing means for detecting the presence of a sample container in said fixture.

7. The measuring apparatus of claim 6 wherein said fixture includes a plurality of wells for receiving respective sample containers; a needle assembly extending into the bottom of each sample well in said fixture for puncturing said sample containers when the sample containers are inserted into said fixture; a rotary valve having a plurality of inlets connected to respective needle assemblies a single outlet connected to said second inlet line in said fluid sampling circuit; and means for indexing said rotary valve to sequentially feed each blood plasma sample into said fluid sampling circuit.

8. The measuring apparatus of claim 1 further including a reaction unit disposed along said reaction tube for heating the reaction mixture as it flows through said reaction tube.

9. The measuring apparatus of claim 8 wherein said reaction unit comprises first and second mating blocks constructed of a heat-conducting material; a serpentine groove formed in a mating surface of one of said first and second blocks, wherein said reaction tube passes through said serpentine groove; and a heating element for heating said mating blocks.

10. The measuring apparatus of claim 9 further including a thermocouple for measuring the temperature of said mating blocks; and a control means responsive to the temperature as measured by said thermocouple to regulate the heat applied by said heating elements.

11. A flow analysis method for measuring, in a blood sample containing a plurality of lipoprotein classes, the distribution of cholesterol among said lipoprotein classes, comprising:
  a) separating the blood sample in a sample container into two or more fractions representing different lipoprotein classes to form a gradient;
  b) providing a continuous, non-segmented stream of reagent which continuously flows from a reagent source to a detector;
  c) introducing each sample fraction in said gradient into the reagent streams, comprising programming a controller to open a first inlet line connected to said sample container wherein said first line feeds the blood sample into the reagent stream in a continuous succession upstream from the detector;
  d) reacting each sample fraction with the reagent as the sample fractions flow from a reaction tube toward said detector to produce a measurable reaction signal indicative of the cholesterol concentration in each sample fraction of the gradient while controlling dispersion of the sample fractions within the reagent stream;
  e) detecting the end of the sample with a meniscus detector disposed in the first inlet line before introduction of the sample into said reagent stream;
  f) backflushing a said inlet line with a wash solution in response to detection of the end of the sample by said meniscus detector, comprising programming a said controller to open a second inlet line connected to source of said wash solution while said first inlet line remains open, and close said first inlet line containing said sample a predetermined time period after the second inlet line is open, wherein said second inlet line remains open to deliver said wash solution to said reaction tube.

12. The flow analysis method of claim 11 wherein the step of separating the blood sample into two or more fractions includes centrifuging the blood sample to form a density gradient.

13. An apparatus for measuring the cholesterol distribution among plasma lipoproteins in a blood sample separated into two or more gradients containing said plasma lipoproteins, said apparatus comprising:
  a) a reaction tube having an inlet and an outlet;
  b) a reagent supply connected to the inlet of said reaction tube for providing a continuous, non-segmented stream of reagent in said reaction tube;
  c) a fluid sampling circuit for alternately introducing a baseline fluid and said blood plasma sample into said reaction tube to be mixed with said continuous reagent stream, said fluid sampling circuit including:
    i) a first inlet line connected to a source of a baseline fluid,
    ii) a second inlet line connected to a sample container containing said blood plasma samples, and
    iii) an outlet line connected to said reaction tube for alternately feeding said baseline fluid and said blood plasma sample into said reaction tube;
  d) sensing means disposed along said second inlet line for detecting the end of said blood plasma sample;
  e) an electrical controller for selectively controlling the flow of said baseline fluid and said blood plasma sample, said controller programmed to:
    i) open said second inlet line to feed the blood plasma sample into said reaction tube,
    ii) open said first inlet line when the end of said sample is detected by said sensing means while said second inlet line remains open to back-flush said second inlet line with said baseline fluid, and
    iii) close said second inlet line a predetermined time period after said first inlet line is opened while said first inlet line remains open to deliver baseline fluid to said reaction tube;
  (f) a detector connected to the outlet of said reaction tube for measuring a characteristic of the fluid flowing through said detector indicative of the cholesterol concentration in said fluid;
  g) a fixture for simultaneously receiving and holding a plurality of sample containers, each of which contains a separate blood plasma sample; and
  h) means for automatically and sequentially feeding said blood plasma samples into said fluid sampling circuit, wherein said electrical controller is programmed to close said first inlet line and open said second inlet line to start the flow of said blood plasma sample through said fluid sampling circuit in response to detection of a sample container in said fixture.

14. The measuring apparatus of claim 13 further including a needle assembly including a flow-through puncturing needle for puncturing said sample containers in said fixture and feeding said samples into said fluid sampling circuit; and indexing means for indexing said fixture to position said sample tubes in alignment with said needle assembly.

15. The measuring apparatus of claim 14 wherein said needle assembly is movable between an extended position to puncture said sample containers and a retracted position.

16. The measuring apparatus of claim 13 further including sensing means for detecting the presence of a sample container in said fixture.

17. The measuring apparatus of claim 16 wherein said fixture includes a plurality of wells for receiving respective sample containers; a needle assembly extending into the bottom of each sample well in said fixture for puncturing said sample containers when the sample containers are inserted into said fixture; a rotary valve having a plurality of inlets connected to respective needle assemblies; a single outlet connected to said second inlet line in said fluid sampling circuit; and means for indexing said rotary valve to sequentially feed each blood plasma sample into said fluid sampling circuit.

18. The measuring apparatus of claim 13 further including a reaction unit disposed along said reaction tube for heating the reaction mixture as it flows through said reaction tube.

19. The measuring apparatus of claim 18 wherein said reaction unit comprises first and second mating blocks constructed of a heat-conducting material; a serpentine groove formed in a mating surface of one of said first and second blocks, wherein said reaction tube passes through said serpentine groove; and a heating element for heating said mating blocks.

20. The measuring apparatus of claim 19 further including a thermocouple for measuring the temperature of said mating conducting blocks; and a control means responsive to the temperature as measured by said thermocouple to regulate the heat applied by said heating element.

21. A flow analysis method for measuring, in a blood sample containing a plurality of lipoprotein classes, the distribution of cholesterol among said lipoprotein classes, comprising:

a) separating the blood sample in a sample container into two or more fractions representing different lipoprotein classes to form a gradient;

b) receiving and holding the sample container in a fixture;

c) providing a continuous, non-segmented stream of reagent which continuously flows from a reagent source to a detector;

d) detecting the presence of the sample container In the fixture;

e) upon detecting the presence of the sample container in the fixture, automatically and sequentially introducing each sample fraction in the gradient into a reagent stream, comprising programming a controller to open a first inlet line connected to said sample container wherein said first inlet line feed the blood sample into the reagent stream in a continuous succession upstream from the detector;

f) reacting each sample fraction with the reagent as the sample fractions flow from a reaction tube toward the detector to produce a measurable reaction signal indicative of the cholesterol concentration in each sample fraction of the gradient while controlling dispersion of the sample fractions within the reagent stream;

g) detecting the end of the sample with a meniscus detector disposed in the first inlet line before introduction of the sample into the reagent stream;

h) backflushing said inlet line with a wash solution in response to detection of the end of the sample by said meniscus detector, comprising programming said controller to open a second inlet line connected to a source of said wash solution while said first inlet line remains open and close said first inlet line containing said sample a predetermined time period after the second inlet line is open, wherein said second inlet line remains open to deliver said wash solution to said reaction tube.

* * * * *